(12) United States Patent
Motohara

(10) Patent No.: US 9,762,329 B2
(45) Date of Patent: Sep. 12, 2017

(54) OPTICAL TRANSMISSION MODULE AND IMAGING DEVICE

(71) Applicant: OLYMPUS CORPORATION, Tokyo (JP)

(72) Inventor: Hiroyuki Motohara, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/796,424

(22) Filed: Jul. 10, 2015

(65) Prior Publication Data

US 2015/0318924 A1    Nov. 5, 2015

Related U.S. Application Data

(63) Continuation of application No. PCT/JP2014/050425, filed on Jan. 14, 2014.

(30) Foreign Application Priority Data

Jan. 18, 2013   (JP) ................... 2013-007805

(51) Int. Cl.
*H04B 10/50* (2013.01)
*H04B 10/25* (2013.01)
(Continued)

(52) U.S. Cl.
CPC ....... *H04B 10/501* (2013.01); *A61B 1/00013* (2013.01); *G02B 6/4202* (2013.01);
(Continued)

(58) Field of Classification Search
CPC .................. A61B 1/00013; H04B 10/501
(Continued)

(56) References Cited

U.S. PATENT DOCUMENTS

2004/0194546 A1* 10/2004 Kanehori ............. G01N 27/225
                                                     73/335.04
2006/0240586 A1* 10/2006 Kobayashi ............. H01J 37/224
                                                     438/26
(Continued)

FOREIGN PATENT DOCUMENTS

EP       2 626 002 A1     8/2013
JP     H10-028672 A     2/1998
(Continued)

OTHER PUBLICATIONS

Extended Supplementary European Search Report dated Mar. 22, 2016 from related European Application No. 14 74 0612.8.
(Continued)

*Primary Examiner* — Oommen Jacob
(74) *Attorney, Agent, or Firm* — Scully, Scott, Murphy & Presser, P.C.

(57) ABSTRACT

An optical transmission module includes: a photoelectric conversion element that converts an electrical signal to an optical signal; a photoelectric conversion element-driving IC that drives the photoelectric conversion element; an optical fiber that transmits the optical signal; a guide holding member that holds the optical fiber; a cable that supplies power to at least one of the photoelectric conversion element and the photoelectric conversion element-driving IC; and a substrate on which the photoelectric conversion element and the photoelectric conversion element-driving IC are mounted. The substrate has first and second planes which are perpendicular to each other. The photoelectric conversion element is mounted on the first plane. The optical fiber is connected to a back side of the first plane. An optical axis of the optical fiber is perpendicular to the first plane. The cable is connected to the second plane in parallel with the optical axis of the optical fiber.

8 Claims, 15 Drawing Sheets

(51) Int. Cl.
*G02B 6/42* (2006.01)
*A61B 1/00* (2006.01)
*H01S 5/183* (2006.01)
*H01S 5/022* (2006.01)

(52) U.S. Cl.
CPC ......... *G02B 6/4259* (2013.01); *G02B 6/4279* (2013.01); *G02B 6/4281* (2013.01); *H04B 10/2504* (2013.01); *H01L 2224/16* (2013.01); *H01S 5/02272* (2013.01); *H01S 5/02284* (2013.01); *H01S 5/183* (2013.01)

(58) Field of Classification Search
USPC .......................................... 398/200, 188, 88
See application file for complete search history.

(56) References Cited

U.S. PATENT DOCUMENTS

| | | | | |
|---|---|---|---|---|
| 2007/0266788 | A1* | 11/2007 | Kim | G01M 5/0033 73/588 |
| 2009/0097802 | A1* | 4/2009 | Tamura | G02B 6/4201 385/85 |
| 2009/0273005 | A1* | 11/2009 | Lin | H01L 33/486 257/99 |
| 2010/0031994 | A1* | 2/2010 | Varghese | H01L 31/06875 136/244 |
| 2010/0074581 | A1 | 3/2010 | Tanobe et al. | |
| 2012/0138117 | A1* | 6/2012 | Krajewski | H01L 31/0201 136/244 |
| 2012/0257852 | A1* | 10/2012 | Ogawa | G02B 6/4201 385/14 |
| 2013/0182099 | A1 | 7/2013 | Nakamura | |
| 2015/0318924 | A1* | 11/2015 | Motohara | G02B 6/4259 398/200 |

FOREIGN PATENT DOCUMENTS

| | | |
|---|---|---|
| JP | 2002-304758 A | 10/2002 |
| JP | 2006-141726 A | 6/2006 |
| JP | 2008-118568 A | 5/2008 |
| JP | 2008-279168 A | 11/2008 |
| JP | 2009-098343 A | 5/2009 |
| JP | 2011-050497 A | 3/2011 |
| JP | 2012-226342 A | 11/2012 |
| WO | 2005/057262 A1 | 6/2005 |
| WO | 2012/046856 A1 | 4/2012 |
| WO | WO 2012/043187 A1 | 4/2012 |

OTHER PUBLICATIONS

International Search Report dated Mar. 4, 2014 issued in PCT/JP2014/050425.
Japanese Office Action dated Jul. 4, 2017 in Japanese Patent Application No. 2013-007805.

\* cited by examiner

OPTICAL TRANSMISSION MODULE AND IMAGING DEVICE

CROSS-REFERENCE TO RELATED APPLICATIONS

This application is a continuation of PCT international application Ser. No. PCT/JP2014/050425 filed on Jan. 14, 2014 which designates the United States, incorporated herein by reference, and which claims the benefit of priority from Japanese Patent Application No. 2013-007805, filed on Jan. 18, 2013, incorporated herein by reference.

BACKGROUND

1. Technical Field

The disclosure relates to an optical transmission module and an imaging device including the optical transmission module.

2. Related Art

Conventionally, a medical endoscope makes it possible to observe a lesion by inserting an insertion portion deep into a body, and, if necessary, makes it possible to inspect and treat an inside of the body by simultaneously using a treatment tool. As such an endoscope, there is an endoscope including an imaging device including an image sensor, such as a CCD, at a distal end of the insertion portion. Recently, an image sensor having a large number of pixels is developed for further clear image observation, and use of the image sensor having a large number of pixels for the endoscope is considered. When the endoscope uses the image sensor having a large number of pixels, an optical transmission module needs to be incorporated into the endoscope for high-speed signal transmission between the image sensor and a signal processing device. In order to reduce a burden on a patient and secure observation view, the distal end of the insertion portion of the endoscope is required to have a minimum outer diameter and length, and an optical element module as a hard portion constituting an optical transmission module incorporated into the endoscope also needs to have a minimum width and length.

As a technology about the optical transmission module for conversion between an optical signal and an electrical signal, an optical module is disclosed in which a ferrule for holding an optical fiber is positioned and fixed by a positioning device to a flexible substrate on which a light emitting/receiving element and an electronic component are mounted (For example, see Japanese Patent Application Laid-open No. 2009-98343).

SUMMARY

In some embodiments, an optical transmission module includes: a photoelectric conversion element configured to convert an electrical signal to an optical signal; a photoelectric conversion element-driving IC configured to drive the photoelectric conversion element; an optical fiber configured to transmit the optical signal emitted from the photoelectric conversion element; a guide holding member configured to position and hold the optical fiber; a cable configured to supply power or a signal to at least one of the photoelectric conversion element and the photoelectric conversion element-driving IC; and a substrate on which the photoelectric conversion element and the photoelectric conversion element-driving IC are mounted. The substrate has at least a first plane and a second plane. The first plane and the second plane are perpendicular to each other. The photoelectric conversion element is mounted on the first plane. The optical fiber is connected to a back side of the first plane through the guide holding member such that an optical axis of the optical fiber is perpendicular to the first plane. The cable is directly connected to the second plane in parallel with the optical axis of the optical fiber.

In some embodiments, an imaging device includes: a photoelectric conversion element configured to convert an electrical signal to an optical signal; a photoelectric conversion element-driving IC configured to drive the photoelectric conversion element; an optical fiber configured to transmit the optical signal emitted from the photoelectric conversion element; a guide holding member configured to position and hold the optical fiber; a cable configured to supply power or a signal to at least one of the photoelectric conversion element and the photoelectric conversion element-driving IC; an image sensor configured to acquire an image signal upon imaging; and a substrate on which the photoelectric conversion element, the photoelectric conversion element-driving IC, and the image sensor are mounted. The substrate has a first plane, a second plane, and a third plane. The first plane and the second plane are perpendicular to each other. The second plane and the third plane are perpendicular to each other. The first plane and the third plane are parallel to each other. The photoelectric conversion element is mounted on the first plane. The image sensor is mounted on the third plane. The optical fiber is connected to a back side of the first plane through the guide holding member such that an optical axis of the optical fiber is perpendicular to the first plane. The cable is directly connected to the second plane in parallel with the optical axis of the optical fiber.

The above and other features, advantages and technical and industrial significance of this invention will be better understood by reading the following detailed description of presently preferred embodiments of the invention, when considered in connection with the accompanying drawings.

DETAILED DESCRIPTION

Modes for carrying out the present invention (hereinafter referred to as "embodiments") will be described below with reference to the accompanying drawings. The present invention is not limited to the following embodiments. The same reference signs are used to designate the same elements throughout the drawings. The drawings are schematically shown, and a relationship between a thickness and a width of each member, a ratio of the members, or the like may be different from actual ones. Portions having different dimensional relationships or ratios from each other may be included among the drawings.

First Embodiment

Figure 1:
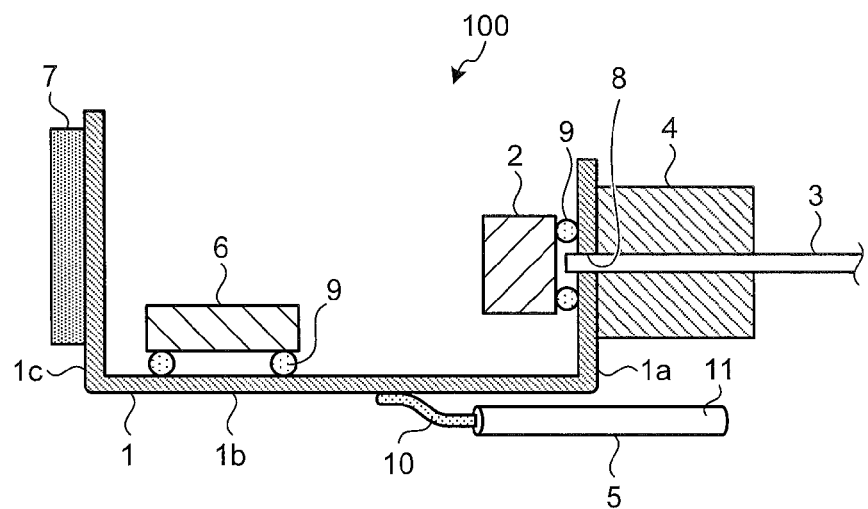
FIG. 1 is a cross-sectional view of an optical transmission module according to a first embodiment of the present invention.
Figure 2:
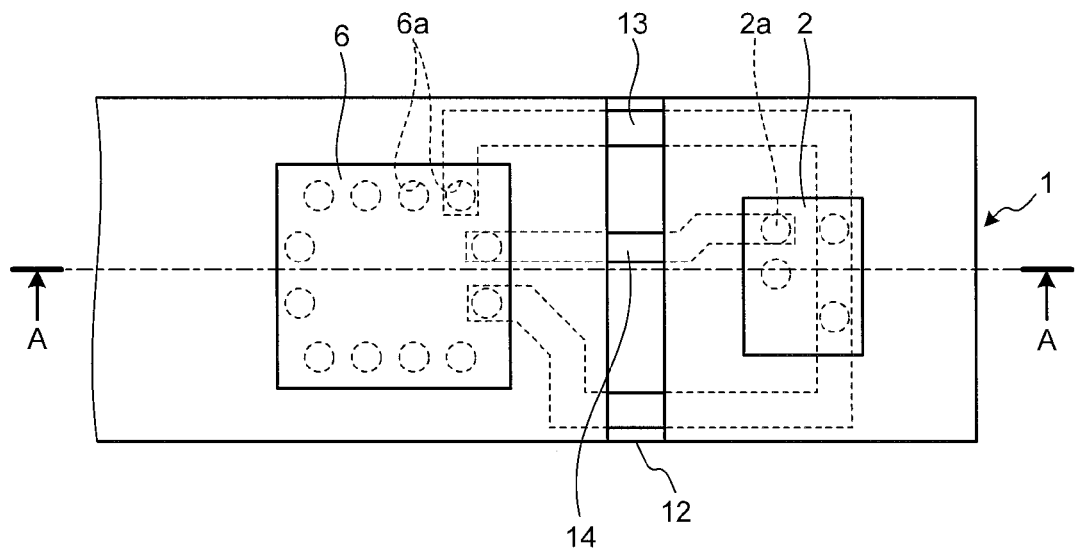
FIG. 2 is a plan view of a substrate used for the optical transmission module of FIG. 1, the substrate being unbent.
Figure 3:
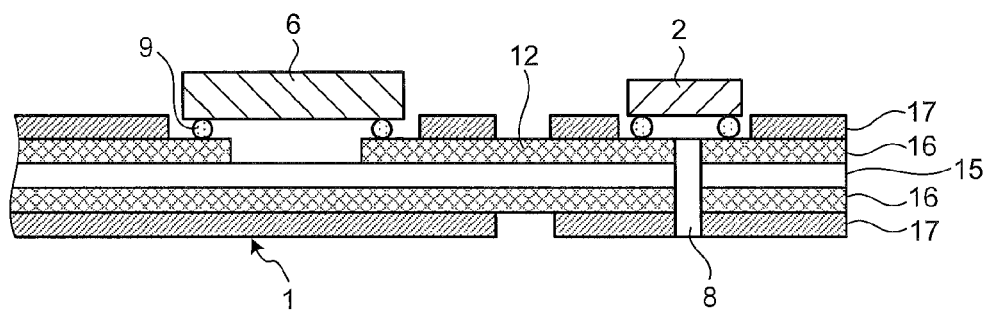
FIG. 3 is a cross-sectional view of the substrate taken along the line A-A of FIG. 2.
Figure 4:
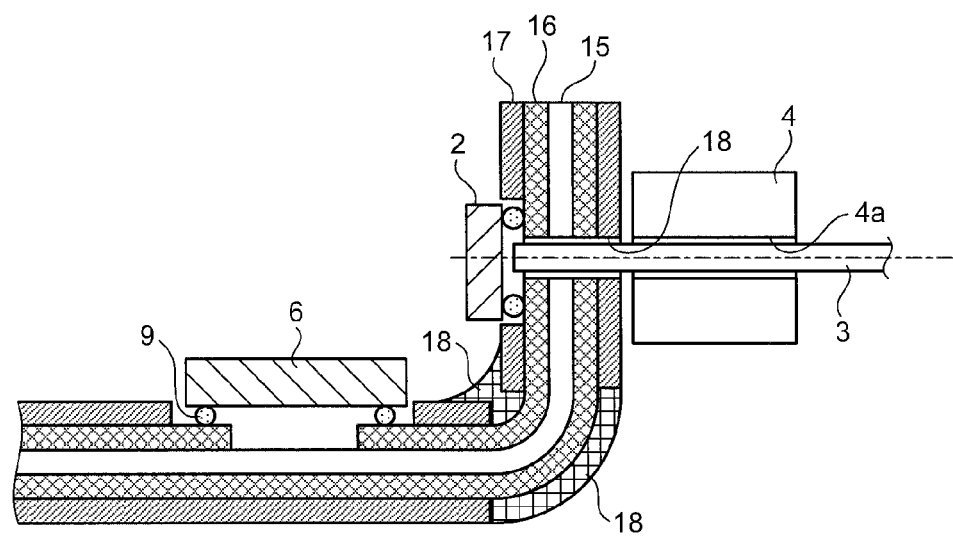
FIG. 4 is a cross-sectional view of the substrate of FIG. 2, the substrate being bent.

FIG. 1 is a cross-sectional view of an optical transmission module according to a first embodiment of the present invention. FIG. 2 is a plan view of a substrate used for the optical transmission module of FIG. 1, the substrate being unbent. FIG. 3 is a cross-sectional view of the substrate taken along the line A-A of FIG. 2. FIG. 4 is a cross-sectional view of the substrate of FIG. 2, the substrate being bent.

An optical transmission module 100 according to a first embodiment of the present invention includes a first substrate 1, a vertical cavity surface emitting laser (hereinafter referred to as VCSEL) 2 as a photoelectric conversion element, an optical fiber 3, a guide holding member 4, a cable 5, and a VCSEL-driving IC 6 as a photoelectric conversion element-driving IC. The optical transmission module 100 according to the present first embodiment functions as an imaging device including an image sensor 7.

The first substrate 1 used in the first embodiment is a bendable substrate such as flexible printed circuits (hereinafter referred to as FPC). The first substrate 1 includes a first plane 1a on which the photoelectric conversion element is mounted, a second plane 1b on which the photoelectric conversion element-driving IC is mounted, and a third plane 1c on which the image sensor 7 is mounted. The first plane 1a and the second plane 1b are perpendicular to each other, and the third plane 1c is perpendicular to the second plane 1b, and parallel to the first plane 1a.

As illustrated in FIGS. 2 and 3, the first substrate 1 includes a base member 15 including a polyimide or the like, metal wires 16 for transmitting an electrical signal, and resist 17. The first substrate 1 has a substrate surface on which the VCSEL 2 and the VCSEL-driving IC 6 are flip-chip bonded by an Au bump 9 or the like. The VCSEL 2 converts an electrical signal of an image captured by the image sensor 7 into an optical signal. The VCSEL-driving IC 6 drives the VCSEL 2. The first substrate 1 has a bent portion 14 in which the resist 17 is removed from the front and back sides of the substrate, and the metal wires 16 passing through the bent portion 14 are disposed perpendicular to the bent portion 14. The resist is removed from the front and back sides of the bent portion 14, so that resist peeling, which may be caused upon bending the FPC, can be inhibited.

Connection electrodes 2a and 6a are formed in the VCSEL 2 and the VCSEL-driving IC 6, respectively, and the connection electrodes 2a and 6a are connected by a signal line 12 and a GND line 13. The metal wires 16 such as the GND line 13 passing through the bent portion 14 are preferably wired axisymmetric about, a substrate axis perpendicular to the bent portion 14. The GND line 13 is preferably wired axisymmetric about the substrate axis. The metal wires 16 such as the GND line 13 and the signal line 12 passing through the bent portion 14 are wired axisymmetric about the substrate axis perpendicular to the bent portion 14, so that generation of distortion upon bending the FPC can be minimized.

After the VCSEL 2 and the VCSEL-driving IC 6 are mounted on the first substrate 1, the optical fiber 3 and the guide holding member 4 are connected to the first substrate 1. The optical fiber 3 is connected to the first plane 1a through the guide holding member 4 so that an optical axis of the optical fiber 3 is perpendicular to the first plane 1a. The guide holding member 4 has a columnar through-hole 4a having substantially the same diameter as the outer diameter of the optical fiber 3 to be held. The guide holding member 4 is mounted on the first substrate 1, for example, by applying an adhesive to a mounting surface of the first substrate 1, subsequently mounting the guide holding member 4 on the adhesive by an apparatus such as a bonder, and hardening the adhesive. The through-hole 4a may have a square columnar shape in addition to the columnar shape, as far as holding the optical fiber 3 on the inner surface thereof. A material of the guide holding member 4 is selected from ceramic, Si, glass, and a metal member such as SUS stainless steel.

The first substrate 1 has a hole portion 8 for transmission of an optical signal from the VCSEL 2 to the optical fiber 3. The hole portion 8 has an inner diameter formed equal to or slightly larger than the inner diameter of the through-hole 4a. The optical fiber 3 is inserted into the through-hole 4a of the guide holding member 4 and mounted on the first substrate 1. The optical fiber 3 receives light emitted from a light emitting unit of the VCSEL 2 through the hole portion 8.

In mounting the VCSEL 2 on the first substrate 1, a dual-view optical system is used to align the center of the light emitting unit of the VCSEL 2 and the center of the hole portion 8 so that the hole portion 8 is positioned immediately under the light emitting unit. Further, in mounting the guide holding member 4 to the first substrate 1, the dual-view optical system is used to align the center of the light emitting unit of the VCSEL 2 and the center of the through-hole 4a. The optical fiber 3 is inserted into the through-hole 4a to the vicinity of the light emitting unit of the VCSEL 2 through the hole portion 8, and bonded to the guide holding member 4 with an adhesive at a position to which light output from the light emitting unit is efficiently input. For easy bonding of the optical fiber 3, the light emitting unit and an end surface of the optical fiber 3 are preferably brought into contact and bonded.

After mounting the optical fiber 3 and the guide holding member 4 on the first substrate 1, the first substrate 1 is bent at the bent portion 14, and reinforced and bonded with an adhesive 18, as illustrated in FIG. 4. Owing to the reinforcement and bonding with the adhesive 18, the FPC is secured to have a substantially perpendicular bending angle. Therefore, variation in bending angle is minimized to reliably position the optical transmission module 100 within an arbitrary projection plane.

The optical fiber 3 has the other end surface connected to a light reception module not illustrated. The light reception module includes a light receiving element and a transimpedance amplifier. The light receiving element is a photodiode (hereinafter referred to as PD) receiving the optical signal output from the VCSEL 2 for photoelectric conversion. The transimpedance amplifier performing impedance conversion and amplification on a current signal obtained by the photoelectric conversion, and outputs the current signal as a voltage signal. The light reception module is further connected to an external signal processing circuit through the transimpedance amplifier.

The cable 5 includes a core 10 formed by a conductor including copper or the like, and an insulation layer 11 externally covering the outer periphery of the core 10. The core 10 of the cable 5 is electrically connected by an electrically conductive material such as solder or gold (Au) to a connection electrode, not illustrated, formed on the back side of the second plane 1b of the first substrate 1 on which the VCSEL-driving IC 6 is mounted. The cable 5 is connected to the second plane 1b in parallel with the optical axis of the optical fiber 3, therefore the optical transmission module 100 according to the first embodiment can have a reduced height.

In the optical transmission module 100 according to the first embodiment, the resist is removed from the bent portion 14 of the FPC so that resist peeling caused by bending the FPC can be prevented, and the bent portion 14 is bonded and secured with the adhesive 18 so that the first plane 1a and the second plane 1b, and the second plane 1b and the third plane 1c are perpendicular to each other, respectively, so that variation in bending angle of the FPC can be minimized. Further, the VCSEL 2, the VCSEL-driving IC 6, and the image sensor 7 are mounted on the first, second, and third planes 1a, 1b, and 1c being bent surfaces of the FPC, so that the optical transmission module 100 can have a reduced length (length in the direction of the optical axis of the optical fiber 3). Further, the cable 5 is connected to the back side of the second plane 1b in parallel with the optical axis of the optical fiber 3, therefore the optical transmission module 100 according to the first embodiment can have a reduced height (diameter). Still further, in the optical transmission module 100 according to the first embodiment, the VCSEL 2, the VCSEL-driving IC 6, and the image sensor 7 are mounted on one substrate, therefore, a manufacturing process of the optical transmission module 100 can be simplified.

First Modification of First Embodiment

Figure 5:
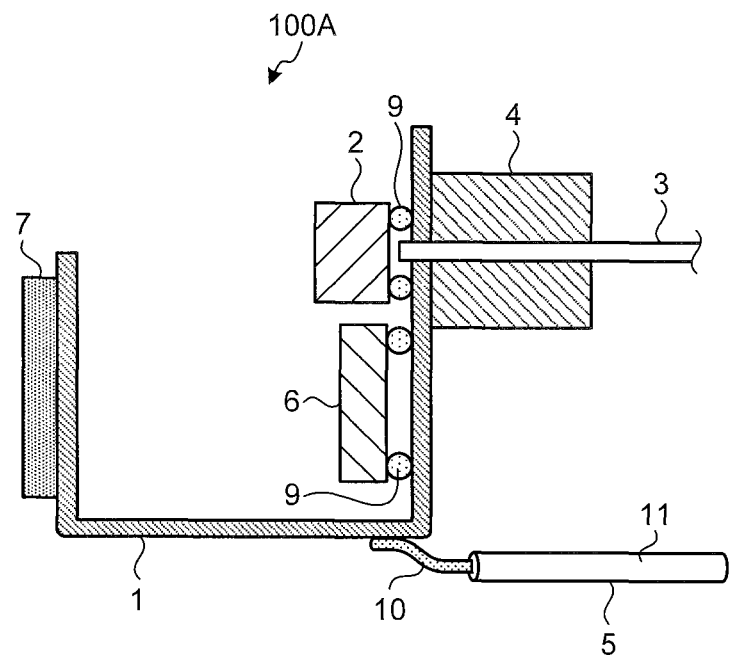
FIG. 5 is a cross-sectional view of an optical transmission module according to a first modification of the first embodiment.

In the optical transmission module 100 according to the first embodiment, the VCSEL 2 is connected to the first plane 1a, and the VCSEL-driving IC 6 is connected to the second plane 1b, but the VCSEL-driving IC 6 may be connected to the first plane 1a, similarly to the VCSEL 2. FIG. 5 is a cross-sectional view of an optical transmission module according to a first modification of the first embodiment of the present invention. In an optical transmission module 100A according to the first modification, the VCSEL 2 and the VCSEL-driving IC 6 are mounted on the first plane 1a of the first substrate 1. In FIG. 5, the VCSEL 2 is mounted above the VCSEL-driving IC 6, but may be positioned otherwise. Further, the VCSEL 2 and the VCSEL-driving IC 6 may be mounted to be arranged side-by-side horizontally. The VCSEL 2 and the VCSEL-driving IC 6 may be disposed on either side between them. According to the first modification, the optical transmission module 100A can have a length further reduced.

Second Embodiment

Figure 6:
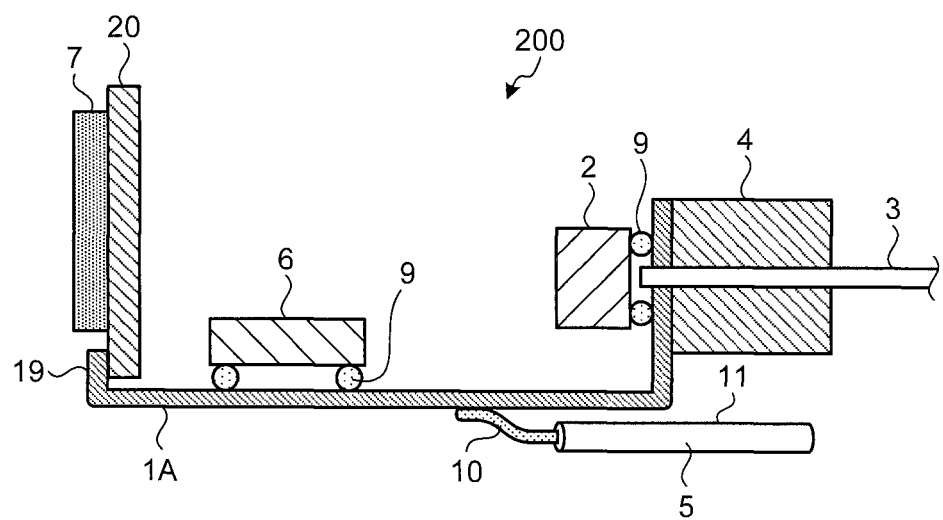
FIG. 6 is a cross-sectional view of an optical transmission module according to a second embodiment.

In the first embodiment, the VCSEL, the VCSEL-driving IC, and the image sensor is mounted on the first substrate, but a second embodiment is different from the first embodiment in that the VCSEL, the VCSEL-driving IC, and the image sensor are mounted on the first substrate and a second substrate, respectively. FIG. 6 is a cross-sectional view of an optical transmission module according to the second embodiment of the present invention.

An optical transmission module 200 includes a first substrate 1A having the first plane 1a on which the VCSEL is mounted, and the second plane 1b on which the VCSEL-driving IC is mounted, and a second substrate 20 on which the image sensor is mounted. The first plane 1a and the second plane 1b are arranged perpendicular to each other, and the second substrate 20 is arranged perpendicular to the second plane 1b, and parallel to the first plane 1a.

The second substrate 20 is a substrate such as a ceramic substrate or an FPC, and the image sensor 7 is mounted as a chip size package (CSP). The first substrate 1A has a connection portion 19 standing perpendicular to the second plane 1b. The first substrate 1A is connected by the connection portion 19 to a surface of the second substrate 20 on which the image sensor 7 is mounted.

In the optical transmission module 200 according to the second embodiment, similarly to the optical transmission module 100 according to the first embodiment, the resist is removed from the bent portion 14 of the FPC, so that resist peeling caused by bending the FPC can be prevented, and the bent portion 14 is bonded and secured with the adhesive 18 so that the first plane 1a and the second plane 1b are perpendicular to each other, so that variation in bending angle of the FPC can be minimized. Further, the VCSEL 2, the VCSEL-driving IC 6, and the image sensor 7 are mounted on the first and second planes 1a and 1b being the bent surfaces of the FPC, and the second substrate 20, respectively. Therefore, the optical transmission module 200 can have a reduced length (length in the direction of the optical axis of the optical fiber 3). Further, the cable 5 is connected to the back side of the second plane 1b in parallel with the optical axis of the optical fiber 3, therefore the optical transmission module 200 according to the second embodiment can have a reduced height (diameter). Still further, in the optical transmission module according to the second embodiment, the image sensor 7 is mounted on the second substrate 20 different from the first substrate 1A. Therefore, a risk such as thermal damage of the image sensor 7 caused by heat generated upon mounting the VCSEL 2 and the VCSEL-driving IC 6 to the first substrate 1A, can be reduced.

First Modification of Second Embodiment

Figure 7:
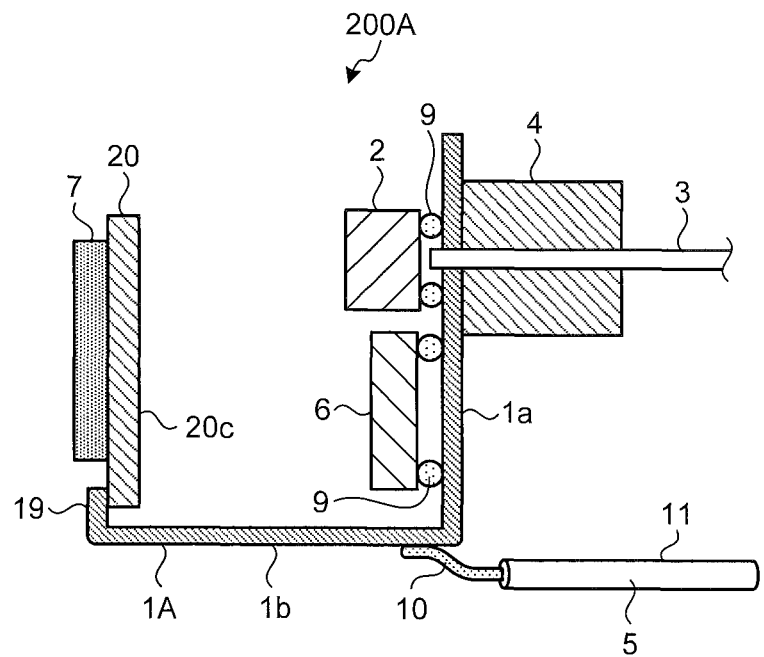
FIG. 7 is a cross-sectional view of an optical transmission module according to a first modification of the second embodiment.

In the optical transmission module 200 according to the second embodiment, the VCSEL 2 is connected to the first plane 1a, and the VCSEL-driving IC 6 is connected to the second plane 1b, but the VCSEL-driving IC 6 may be connected to the first plane 1a, similarly to the VCSEL 2. FIG. 7 is a cross-sectional view of an optical transmission module according to a first modification of the second embodiment of the present invention. In an optical transmission module 200A according to the first modification, the VCSEL 2 and the VCSEL-driving IC 6 are mounted on the first plane 1a of the first substrate 1A. In FIG. 7, the VCSEL 2 is mounted above the VCSEL-driving IC 6, but may be positioned otherwise. Further, the VCSEL 2 and the VCSEL-driving IC 6 may be mounted to be arranged side-by-side horizontally. The VCSEL 2 and the VCSEL-driving IC 6 may be disposed on either side between them. According to the first modification, the optical transmission module 200A can have a length further reduced.

Second Modification of Second Embodiment

Figure 8:
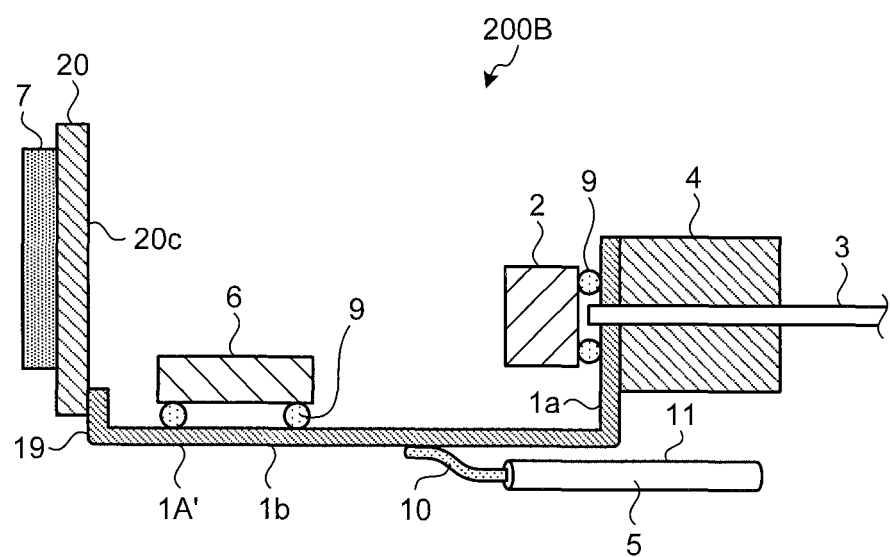
FIG. 8 is a cross-sectional view of an optical transmission module according to a second modification of the second embodiment.

In the optical transmission module 200 according to the second embodiment, the connection portion 19 of the first substrate 1A is connected to the surface of the second substrate 20 on which the image sensor 7 is mounted, but the connection portion 19 may be connected to the back side of the surface on which the image sensor 7 is mounted. FIG. 8 is a cross-sectional view of an optical transmission module according to a second modification of the second embodiment of the present invention. In an optical transmission module 200B according to the second embodiment, the connection portion 19 of the first substrate 1A' is connected to the back side of the surface of the second substrate 20 on which the image sensor 7 is mounted. In the second modification of the second embodiment, the VCSEL 2 is connected to the first plane 1a, and the VCSEL-driving IC 6 is connected to the second plane 1b, but the VCSEL-driving IC 6 may be connected to the first plane 1a, similarly to the VCSEL 2.

Third Modification of Second Embodiment

Figure 9:
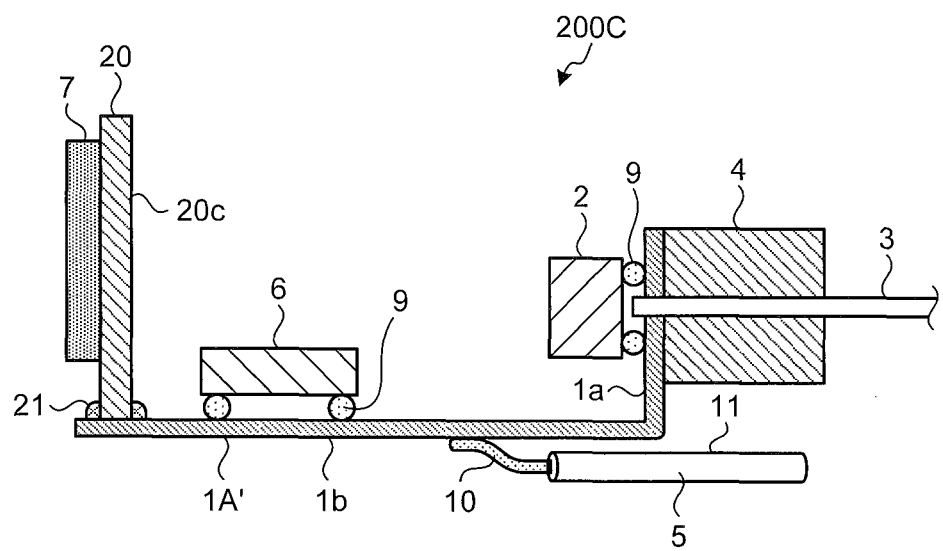
FIG. 9 is a cross-sectional view of an optical transmission module according to a third modification of the second embodiment.

In the optical transmission module 200 according to the second embodiment, the first substrate 1A has a connection portion 19, and the connection portion 19 is connected to the second substrate 20, but the connection may be made without forming the connection portion 19. FIG. 9 is a cross-sectional view of an optical transmission module according to a third modification of the second embodiment of the present invention. In an optical transmission module 200C according to the third modification, an end surface of the second substrate 20 is connected, with an adhesive 21 or the like, to a surface of the first substrate 1A' on which the VCSEL-driving IC 6 is mounted. In the third modification of the second embodiment, the VCSEL 2 is connected to the first plane 1a, and the VCSEL-driving IC 6 is connected to the second plane 1b, but the VCSEL-driving IC 6 may be connected to the first plane 1a, similarly to the VCSEL 2.

Fourth Modification of Second Embodiment

Figure 10:
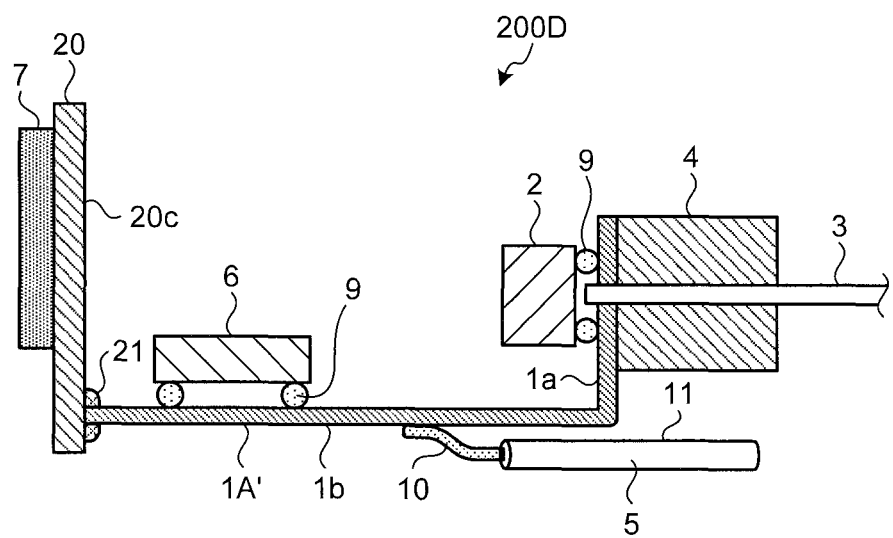
FIG. 10 is a cross-sectional view of an optical transmission module according to a fourth modification of the second embodiment.

In the optical transmission module 200B according to the second modification of the second embodiment, the first substrate 1A' has the connection portion 19, and the connection portion 19 is connected to the second substrate 20, but the connection may be made without forming the connection portion 19. FIG. 10 is a cross-sectional view of an optical transmission module according to a fourth modification of the second embodiment of the present invention. In an optical transmission module 200D according to the fourth modification, an end surface of the first substrate 1A' is connected, with the adhesive 21 or the like, to the back side of the surface of the second substrate 20 on which the image sensor 7 is mounted. In the fourth modification of the second embodiment, the VCSEL 2 is connected to the first plane 1a, and the VCSEL-driving IC 6 is connected to the second plane 1b, but the VCSEL-driving IC 6 may be connected to the first plane 1a, similarly to the VCSEL 2.

Fifth Modification of Second Embodiment

Figure 11:
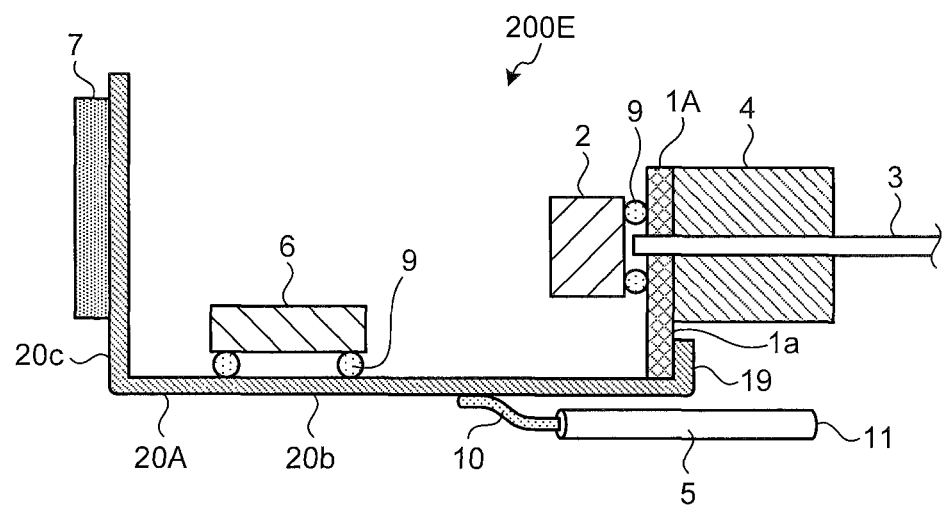
FIG. 11 is a cross-sectional view of an optical transmission module according to a fifth modification of the second embodiment.

In an optical transmission module 200E according to a fifth modification of the second embodiment, the second substrate has the second plane and the third plane perpendicular to each other, and the first substrate has a plate shape. FIG. 11 is a cross-sectional view of the optical transmission module according to the fifth modification of the second embodiment of the present invention. In the optical transmission module 200E according to the fifth modification, a second substrate 20A includes a third plane 20c, a second plane 20b, and the connection portion 19. The image sensor 7 is mounted on the third plane 20c. The VCSEL-driving IC 6 is mounted on the second plane 20b, and the cable 5 is connected to a back side of the second plane 20b. The connection portion 19 is formed to stand perpendicular to the second plane 20b. The second substrate 20A preferably is an FPC. The first substrate 1A is selected from a silicon substrate, an FPC substrate, and the like. In the optical transmission module 200E, the connection portion 19 is connected to the back side of a surface of the first substrate 1A on which the VCSEL 2 is mounted so that the first substrate 1A and the second plane 20b of the second substrate 20A are perpendicular to each other. It is noted that the connection portion 19 may be connected to the surface of the first substrate 1A on which the VCSEL 2 is mounted.

Sixth Modification of Second Embodiment

Figure 12:
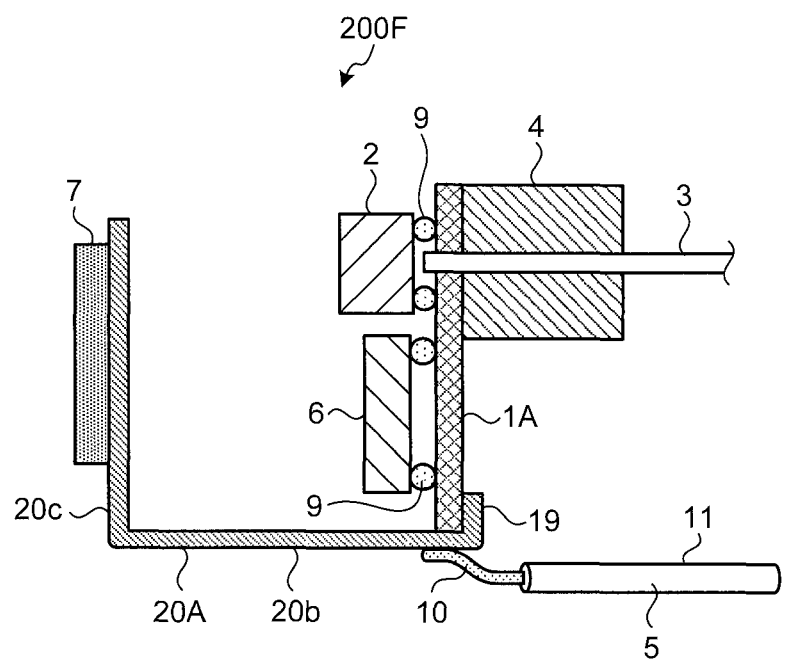
FIG. 12 is a cross-sectional view of an optical transmission module according to a sixth modification of the second embodiment.

In an optical transmission module 200F according to a sixth modification of the second embodiment, the second substrate has the second plane and the third plane perpendicular to each other, and the VCSEL-driving IC is mounted on the first substrate having a plate shape. FIG. 12 is a cross-sectional view of the optical transmission module according to the sixth modification of the second embodiment of the present invention. In the optical transmission module 200F according to the sixth modification, the second substrate 20A includes the third plane 20c on which the image sensor 7 is mounted, the second plane 20b to which the cable 5 is connected, and the connection portion 19. Further, the VCSEL 2 and the VCSEL-driving IC 6 are mounted on the first substrate 1A having a plate shape. In FIG. 12, the VCSEL 2 is mounted above the VCSEL-driving IC 6, but may be positioned otherwise. Further, the VCSEL 2 and the VCSEL-driving IC 6 may be mounted to be arranged side-by-side horizontally. The VCSEL 2 and the VCSEL-driving IC 6 may be disposed on either side between them. Further, the connection portion 19 of the second substrate 20A is formed to stand perpendicular to the second plane 20b. In the optical transmission module 200F, the connection portion 19 is connected to the back side of the surface of the first substrate 1A on which the VCSEL 2 or the like is mounted so that the first substrate 1A and the second plane 20b of the second substrate 20A are perpendicular to each other. It is noted that the connection portion 19 may be connected to the surface of the first substrate 1A on which the VCSEL 2 is mounted.

Third Embodiment

Figure 13:
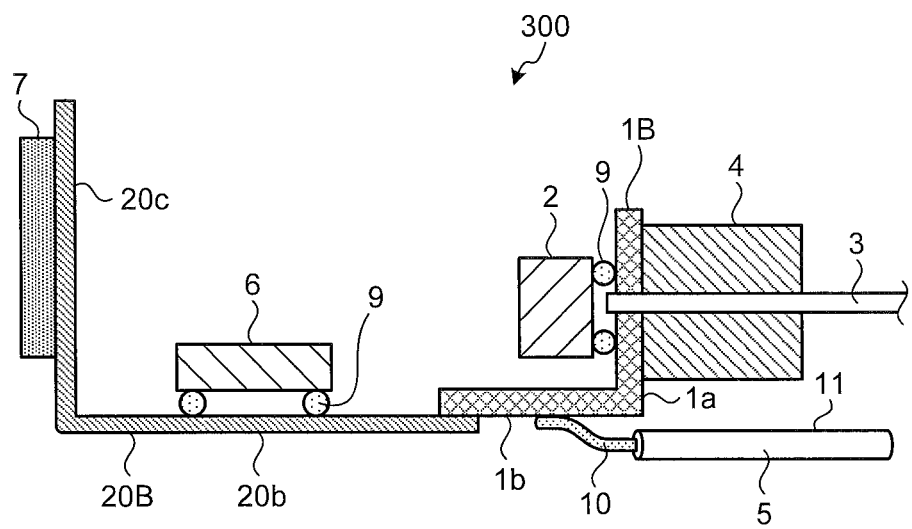
FIG. 13 is a cross-sectional view of an optical transmission module according to a third embodiment.

In the second embodiment, the first substrate having the first plane and the second plane, and the second substrate having a plate shape, or the first substrate having a plate-shape and the second substrate having the second plane and the third plane are connected. However, a third embodiment is different from the second embodiment in that each of the first substrate and the second substrate has the second plane, and the second planes of the first substrate and the second substrate are connected to each other. FIG. 13 is a cross-sectional view of an optical transmission module according to the third embodiment of the present invention.

In an optical transmission module 300 according to the third embodiment, a first substrate 1B has the first plane 1a on which the VCSEL 2 is mounted, and the second plane 1b to which the cable 5 is connected in parallel with the optical axis of the optical fiber 3. Further, a second substrate 20B has the third plane 20c on which the image sensor 7 is mounted, and the second plane 20b on which the VCSEL-driving IC 6 is mounted. The second substrate 20B is preferably the FCP, as in the first substrate 1B. In the optical transmission module 300 according to the third embodiment, the first plane 1a and the second plane 1b are perpendicular to each other, the third plane 20c of the second substrate 20B is perpendicular to the second plane 20b, and parallel to the first plane 1a.

The first substrate 1B and the second substrate 20B are connected so that the second plane 1b of the first substrate 1B overlaps the upper portion of the second plane of the second substrate 20B, that is, the first substrate 1B is connected to the surface of the second plane 20b of the second substrate 20B on which the VCSEL-driving IC 6 is mounted.

In the optical transmission module 300 according to the third embodiment, similarly to the first and second embodiments, the resist is removed from the bent portion 14 of the FPC so that resist peeling caused by bending the FPC can be prevented, and the bent portion 14 is bonded and secured with the adhesive 18 so that the first plane 1a and the second plane 1b are perpendicular to each other, and the second plane 20b and the third plane 20c are perpendicular to each other, so that variation in bending angle of the FPC can be minimized. Further, the VCSEL 2, the VCSEL-driving IC 6, and the image sensor 7 are mounted on the first plane 1a of the first substrate 1B, and the second and third planes 20b and 20c being the bent surfaces of the second substrate 20B, so that the optical transmission module 300 can have a reduced length (length in the direction of the optical axis of the optical fiber 3). Further, the cable 5 is connected to the second plane 1b of the first substrate 1B in parallel with the optical axis of the optical fiber 3, therefore the optical transmission module 300 according to the third embodiment can have a reduced height (diameter). In the present third embodiment, the first substrate 1B is connected to the second substrate 20B so that the second plane 1b of the first substrate 1B overlaps the upper portion of the second substrate 20B, but the second plane 20b may overlap the second plane 1b.

First Modification of Third Embodiment

Figure 14:
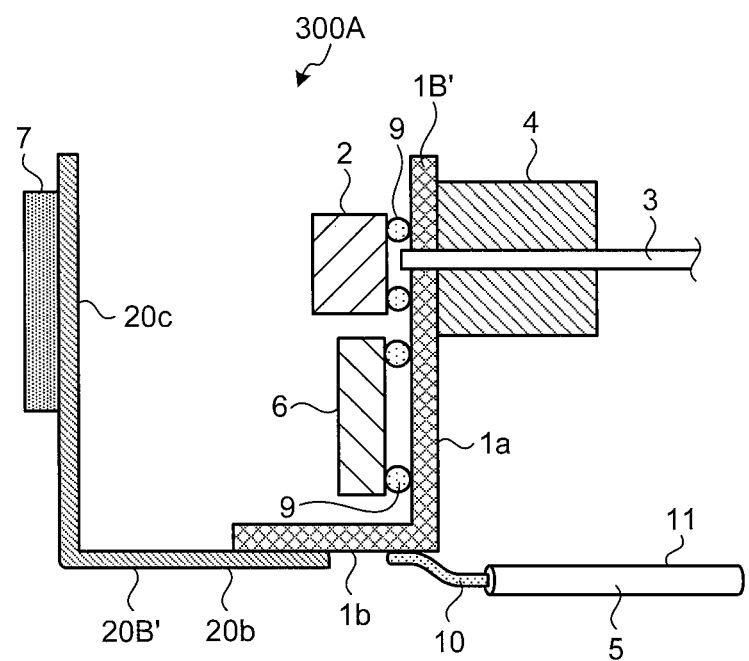
FIG. 14 is a cross-sectional view of an optical transmission module according to a first modification of the third embodiment.

In the optical transmission module 300 according to the third embodiment, the VCSEL 2 is connected to the first plane 1a, and the VCSEL-driving IC 6 is connected to the second plane 20b, but the VCSEL-driving IC 6 may be connected to the first plane 1a, similarly to the VCSEL 2. FIG. 14 is a cross-sectional view of an optical transmission module according to a first modification of the third embodiment of the present invention. In an optical transmission module 300A according to the first modification, the VCSEL 2 and the VCSEL-driving IC 6 are mounted on the first plane 1a of the first substrate 1B'. In FIG. 14, the VCSEL 2 is mounted above the VCSEL-driving IC 6, but may be positioned otherwise. Further, the VCSEL 2 and the VCSEL-driving IC 6 may be mounted to be arranged side-by-side horizontally. The VCSEL 2 and the VCSEL-driving IC 6 may be disposed on either side between them. According to the first modification, the optical transmission module 300A can have a length further reduced. In the first modification, the first substrate 1B is connected to the second substrate 20B' so that the second plane 1b of the first substrate 1B overlaps the upper portion of the second plane 20b of the second substrate 20B', but the second plane 20b may overlap the second plane 1b.

Second Modification of Third Embodiment

Figure 15:
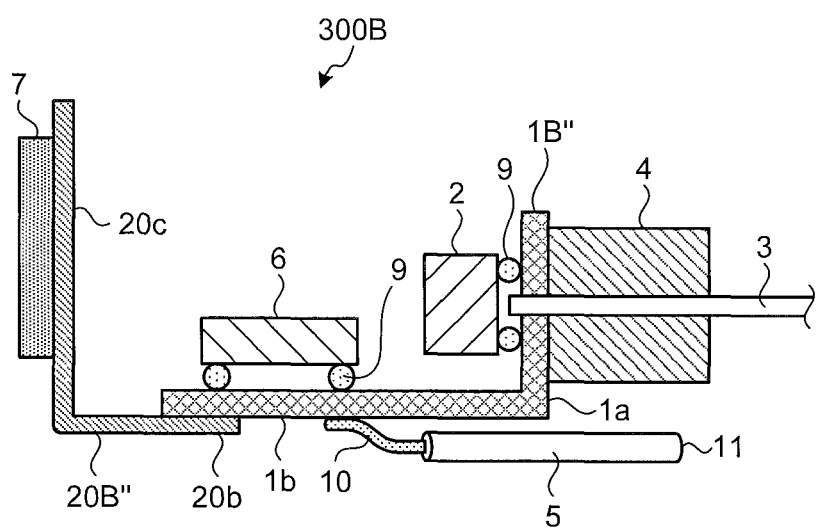
FIG. 15 is a cross-sectional view of an optical transmission module according to a second modification of the third embodiment.

In an optical transmission module 300 according to the third embodiment, the VCSEL-driving IC 6 is mounted on the second plane 20b of the second substrate 20B, but the VCSEL-driving IC 6 may be mounted on the first substrate 1B. FIG. 15 is a cross-sectional view of an optical transmission module according to a second modification of the third embodiment of the present invention. An optical transmission module 300B according to the second modification includes the first substrate 1B" having the first plane 1a on which the VCSEL 2 is mounted, and the second plane 1b on which the VCSEL-driving IC is mounted and the second substrate 20B" having the second plane 20b, and the third plane 20c on which the image sensor 7 is mounted. In the optical transmission module 300B according to the second modification of the third embodiment, the first plane 1a and the second plane 1b are arranged perpendicular to each other, and the third plane 20c of the second substrate 20B" is arranged perpendicular to the second plane 1b, and parallel to the first plane 1a. It is noted that, in the second modification, the second plane 20b of the second substrate 20B" is connected to the back side of the surface of the first substrate 1B" on which the VCSEL-driving IC 6 is mounted, but the second plane 20b may be connected to the surface on which the VCSEL-driving IC 6 is mounted.

Third Modification of Third Embodiment

Figure 16:
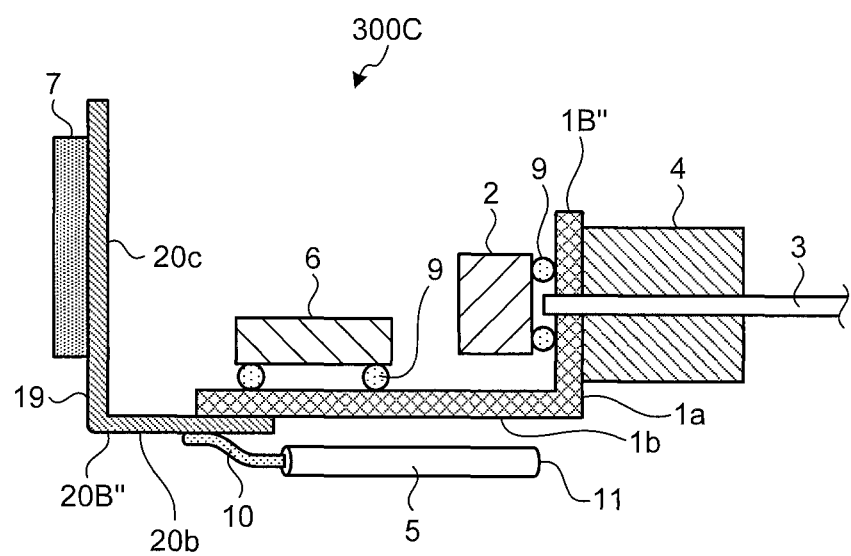
FIG. 16 is a cross-sectional view of an optical transmission module according to a third modification of the third embodiment.

In the optical transmission module 300 according to the third embodiment, the cable 5 is connected to the second plane 1b of the first substrate 1B, but in a third modification of the third embodiment, the cable 5 is connected to the second plane 20*b* of the second substrate 20B". FIG. 16 is a cross-sectional view of an optical transmission module according to the third modification of the third embodiment of the present invention. In an optical transmission module 300C, the cable 5 is connected to the back side of the surface of the second plane 20*b* of the second substrate 20B" on which the VCSEL-driving IC 6 is mounted. In the third modification, the cable 5 for transmitting a signal to the image sensor 7 is connected to the second substrate 20B" on which the image sensor 7 is mounted, so that influence of a noise or the like can be reduced. It is noted that, in the third modification, the second plane 1*b* of the first substrate 1B" is connected to the surface of the second plane 20*b* of the second substrate 20B" on which the VCSEL-driving IC 6 is mounted, but the second plane 1*b* may be connected to the back side of the surface on which the VCSEL-driving IC 6 is mounted.

Fourth Modification of Third Embodiment

Figure 17:
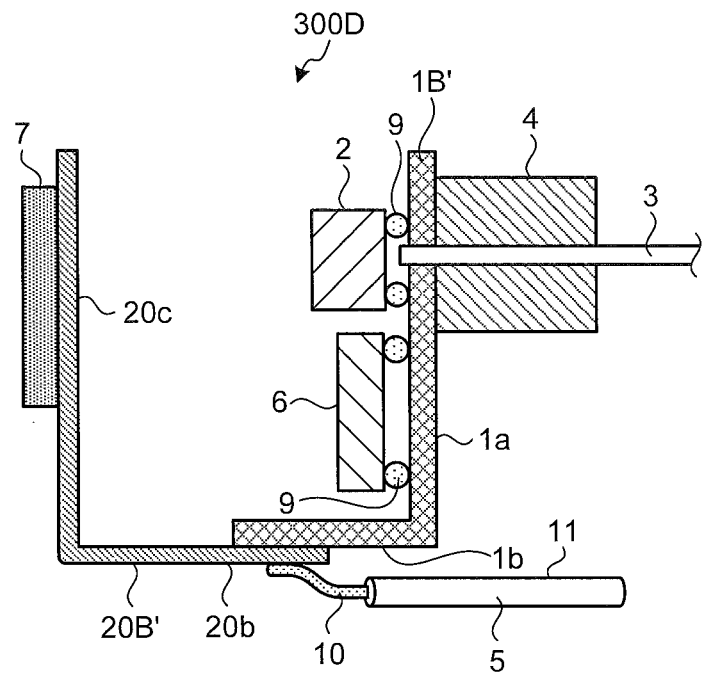
FIG. 17 is a cross-sectional view of an optical transmission module according to a fourth modification of the third embodiment.

In a fourth modification of the third embodiment, the cable 5 is connected to the second plane 20*b* of the second substrate 20B°, and the VCSEL-driving IC 6 is connected to the first plane 1*a* of the first substrate 1B'. FIG. 17 is a cross-sectional view of an optical transmission module according to the fourth modification of the third embodiment of the present invention. In an optical transmission module 300D according to the fourth modification, the cable 5 for transmitting a signal to the image sensor 7 is connected to the second substrate 20B' on which the image sensor 7 is mounted, so that the influence of a noise or the like can be reduced. It is noted that, in the fourth modification, the second plane 1*b* of the first substrate 1B' is connected to the surface of the second plane 20*b* of the second substrate 20B' on which the VCSEL-driving IC 6 is mounted, but the second plane 1*b* may be connected to the back side of the surface on which the VCSEL-driving IC 6 is mounted.

Fifth Modification of Third Embodiment

Figure 18:
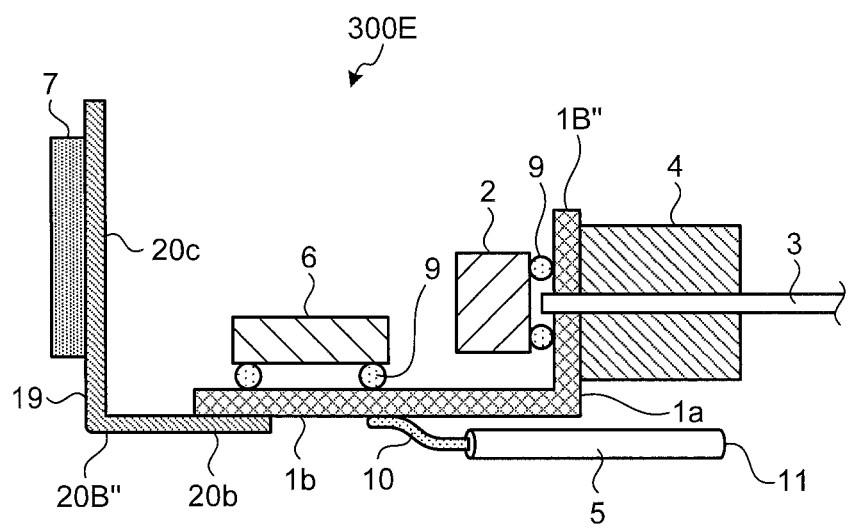
FIG. 18 is a cross-sectional view of an optical transmission module according to a fifth modification of the third embodiment.

In a fifth modification of the third embodiment, the cable 5 is connected to the second plane 20*b* of the second substrate 20B", and the VCSEL-driving IC 6 is connected to the second plane 1*b* of the first substrate 1B". FIG. 18 is a cross-sectional view of an optical transmission module according to the fifth modification of the third embodiment of the present invention. In an optical transmission module 300E according to the fifth modification, the cable 5 for transmitting a signal to the image sensor 7 is connected to the second substrate 20B" on which the image sensor 7 is mounted, so that the influence of a noise or the like can be reduced. It is noted that, in the fifth modification, the second plane 1*b* of the first substrate 1B" is connected to the surface of the second plane 20*b* of the second substrate 20B" on which the VCSEL-driving IC 6 is mounted, but the second plane 1*b* may be connected to the back side of the surface on which the VCSEL-driving IC 6 is mounted.

Fourth Embodiment

Figure 19:
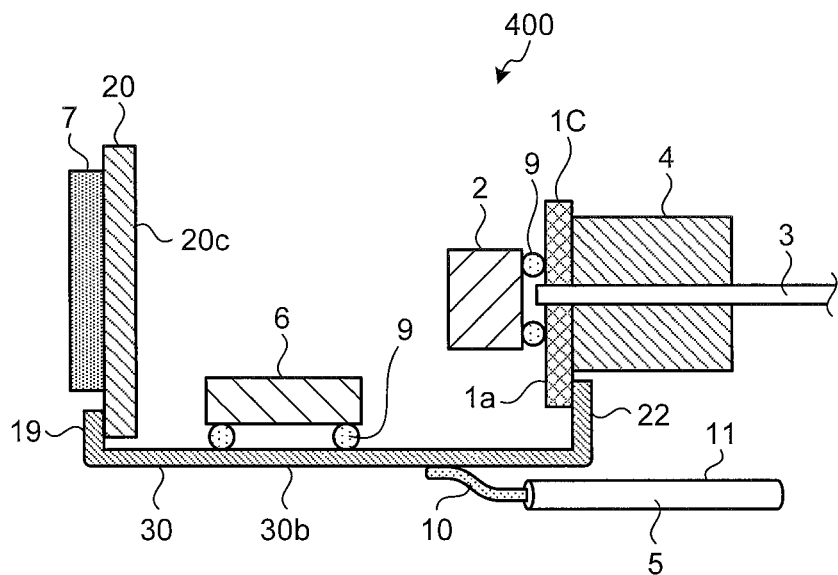
FIG. 19 is a cross-sectional view of an optical transmission module according to a fourth embodiment.

In the first embodiment, the VCSEL 2, the VCSEL-driving IC 6, and the image sensor 7 are mounted on one substrate, but a fourth embodiment is different from the first embodiment in that the VCSEL 2, the VCSEL-driving IC 6, and the image sensor 7 are mounted on three substrates, i.e., the first substrate, the second substrate, and/or a third substrate, respectively. FIG. 19 is a cross-sectional view of an optical transmission module according to the fourth embodiment of the present invention.

An optical transmission module 400 includes a first substrate 1C including the first plane 1*a* on which the VCSEL 2 is mounted, a third substrate 30 having a second plane 30*b* on which the VCSEL-driving IC 6 is mounted, and the second substrate 20 including the third plane 20*c* on which the image sensor 7 is mounted.

The third substrate 30 includes the connection portion 19 and a connection portion 22 for connecting the second substrate 20 and the first substrate 1C, respectively. The connection portions 19 and 22 are perpendicular to the second plane 30*b* of the third substrate 30. The connection portion 19 is connected to a surface of the second substrate 20 on which the image sensor 7 is mounted, and the connection portion 22 is connected to the back side of the surface of the first substrate 1C on which the VCSEL 2 is mounted. The third substrate 30 preferably is an FPC, in view of formation of the connection portions 19 and 22. The bent portions between the connection portions 19 and 22 and a main surface (second plane 30*b*) are preferably formed similarly to the bent portion 14 of the first embodiment. The first substrate 1C and the second substrate 20 are each selected from a ceramic substrate, an FPC, and the like. The substrates are connected by the connection portions 19 and 22 so that the first substrate 1C and the third substrate 30 are perpendicular to each other, the second substrate 20 is perpendicular to the third substrate 30, and parallel to the first substrate 1C.

In the optical transmission module 400 according to the fourth embodiment, similarly to the first to third embodiments, the cable 5 is connected to the second plane 30*b* of the third substrate 30 in parallel with the optical axis of the optical fiber 3, therefore the optical transmission module 300 according to the fourth embodiment can have a reduced height (diameter). Further, the VCSEL 2, the VCSEL-driving IC 6, and the image sensor 7 are mounted on the first plane 1*a* of the first substrate 1C, the second plane 30*b* of the third substrate 30, and the third plane 20*c* of the second substrate 20, which are perpendicular to one another, so that the optical transmission module 400 can have a reduced length (length in the direction of the optical axis of the optical fiber 3).

First Modification of Fourth Embodiment

Figure 20:
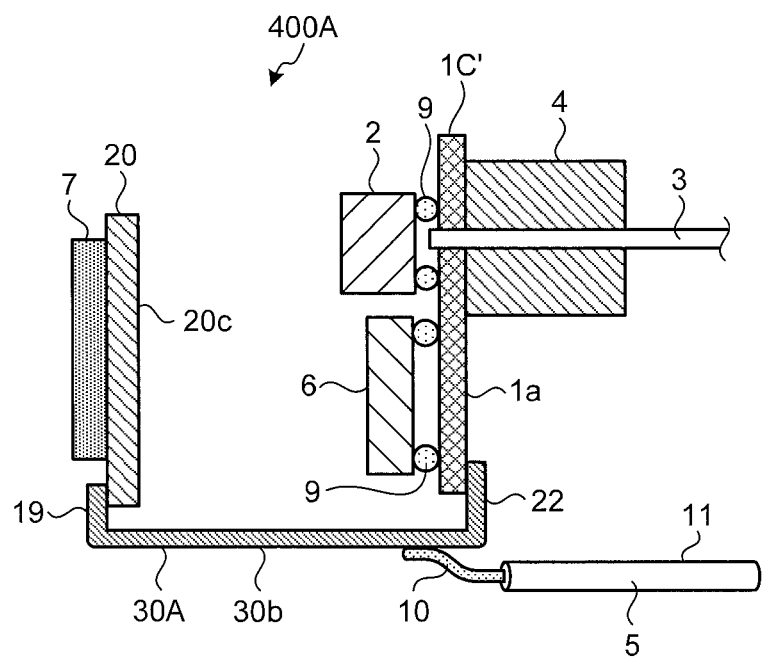
FIG. 20 is a cross-sectional view of an optical transmission module according to a first modification of the fourth embodiment.

In the optical transmission module 400 according to the fourth embodiment, the VCSEL-driving IC 6 is connected to the second plane 30*b* of the third substrate 30, but the VCSEL-driving IC 6 may be connected to the first substrate, similarly to the VCSEL 2. FIG. 20 is a cross-sectional view of an optical transmission module according to a first modification of the fourth embodiment of the present invention. In an optical transmission module 400A according to the first modification, the VCSEL 2 and the VCSEL-driving IC 6 are mounted on the first plane 1*a* of the first substrate 1C'. In FIG. 20, the VCSEL 2 is mounted above the VCSEL-driving IC 6, but may be positioned otherwise. Further, the VCSEL 2 and the VCSEL-driving IC 6 may be mounted to be arranged side-by-side horizontally. The VCSEL 2 and the VCSEL-driving IC 6 may be disposed on either side between them. According to the first modification, the optical transmission module 400A can have a length further reduced in the optical axis direction.

Second Modification of Fourth Embodiment

Figure 21:
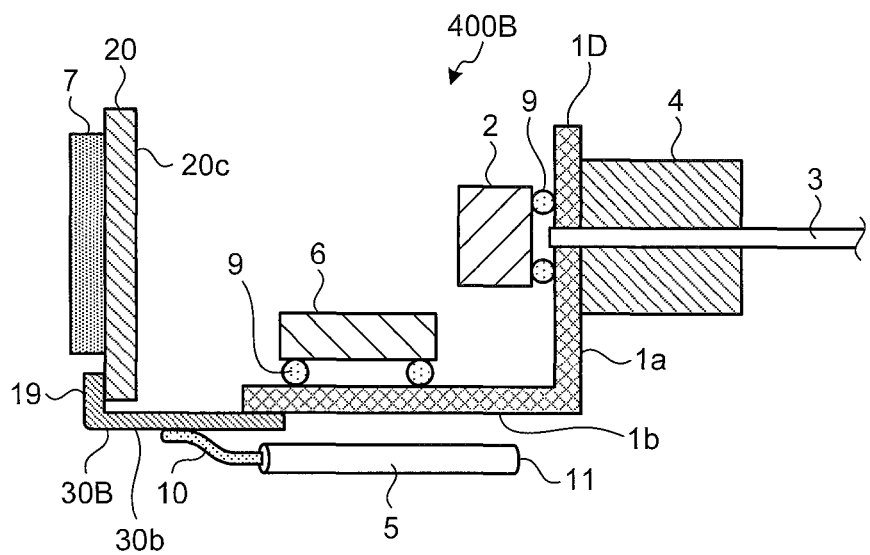
FIG. 21 is a cross-sectional view of an optical transmission module according to a second modification of the fourth embodiment.

In an optical transmission module 400B according to a second modification of the fourth embodiment, the first substrate has the first plane and the second plane, and the VCSEL-driving IC 6 is mounted on the second plane of the first substrate. FIG. 21 is a cross-sectional view of the optical transmission module according to the second modification of the fourth embodiment of the present invention. In the optical transmission module 400B according to the second modification, a first substrate 1D has the first plane 1*a* on which the VCSEL 2 is mounted, and the second plane 1b on which the VCSEL-driving IC 6 is mounted. The first plane 1a and the second plane 1b are perpendicular to each other. The cable 5 is connected to a third substrate 30B in parallel with the optical axis of the optical fiber 3. It is noted that the cable 5 may be connected to the second plane 1b of the first substrate 1D. Further, in the second modification, the third substrate 30B is connected to the second substrate 20 so that the connection portion 19 overlaps the surface of the second substrate 20 on which the image sensor 7 is mounted, and the third substrate 30B and the first substrate 1D are connected to each other so that the second plane 1b of the first substrate overlaps the third substrate 30B. It is noted that the third substrate 30B may be connected through the connection portion 19 to the back side of the surface of the second substrate 20 on which the image sensor 7 is mounted, and the third substrate 30B and the first substrate 1D may be connected to each other so that the third substrate 30B overlaps the second plane 1b of the first substrate.

Third Modification of Fourth Embodiment

Figure 22:
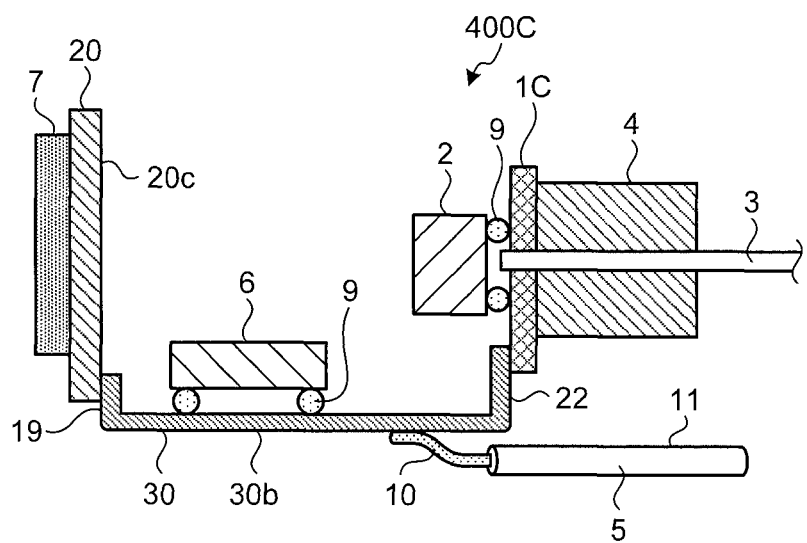
FIG. 22 is a cross-sectional view of an optical transmission module according to a third modification of the fourth embodiment.

An optical transmission module 400C according to a third modification of the fourth embodiment is different from the optical transmission module 400 according to the fourth embodiment in connection of the third substrate with the first and the second substrates through the connection portions 19 and 22. FIG. 22 is a cross-sectional view of the optical transmission module according to the third modification of the fourth embodiment of the present invention. In the optical transmission module 400C according to the third modification, the connection portion 19 standing perpendicular to the second plane 30b of the third substrate 30 is connected to the back side of the surface of the second substrate 20 on which the image sensor 7 is mounted, and the connection portion 22 standing perpendicular to the second plane 30b of the third substrate 30 is connected to the surface of the first substrate 1C on which the VCSEL 2 is mounted. It is noted that the connection portion 19 may be connected to the back side of the surface of the second substrate 20 on which the image sensor 7 is mounted, and the connection portion 22 may be connected to the back side of the surface of the first substrate 1C on which the VCSEL 2 is mounted. Further, the connection portion 19 may be connected to the surface of the second substrate 20 on which the image sensor 7 is mounted, and the connection portion 22 may be connected to the surface of the first substrate 1C on which the VCSEL 2 is mounted.

Fourth Modification of Fourth Embodiment

Figure 23:
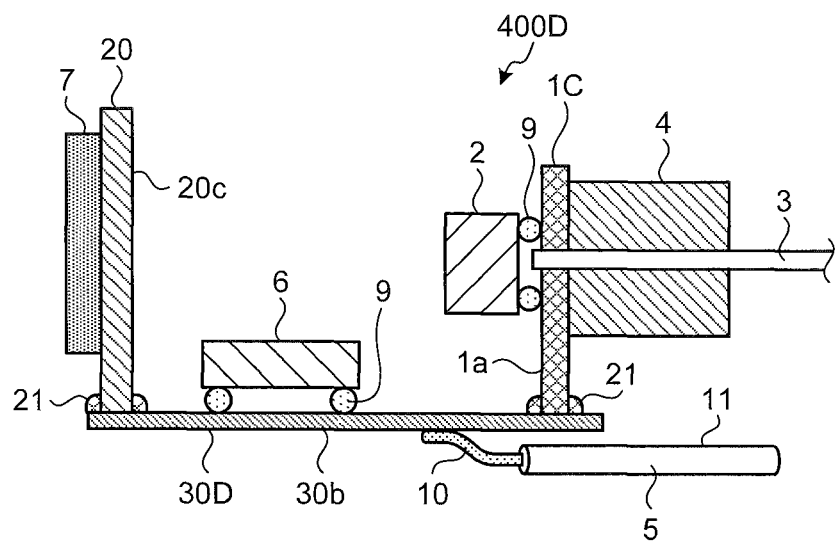
FIG. 23 is a cross-sectional view of an optical transmission module according to a fourth modification of the fourth embodiment.

In an optical transmission module 400D according to a fourth modification of the fourth embodiment, the third substrate, the first substrate, and the second substrate are connected without through the connection portions. FIG. 23 is a cross-sectional view of the optical transmission module according to the fourth modification of the fourth embodiment of the present invention. In the optical transmission module 400D according to the fourth modification, an end of the first substrate 1C is connected with the adhesive 21 to a surface of a third substrate 30D on which the VCSEL-driving IC 6 is mounted so that the third substrate 30D and the first substrate 1C are perpendicular to each other. Further, an end of the second substrate 20 is connected with the adhesive 21 to the surface of the third substrate 30D on which the VCSEL-driving IC 6 is mounted so that the third substrate 30D and the second substrate 20 are perpendicular to each other. It is noted that, in the fourth modification of the fourth embodiment, the VCSEL-driving IC 6 is connected to the second plane 30b of the third substrate 30D, but the VCSEL-driving IC 6 may be mounted on the surface of the first substrate 1C on which the VCSEL 2 is mounted.

Fifth Modification of Fourth Embodiment

Figure 24:
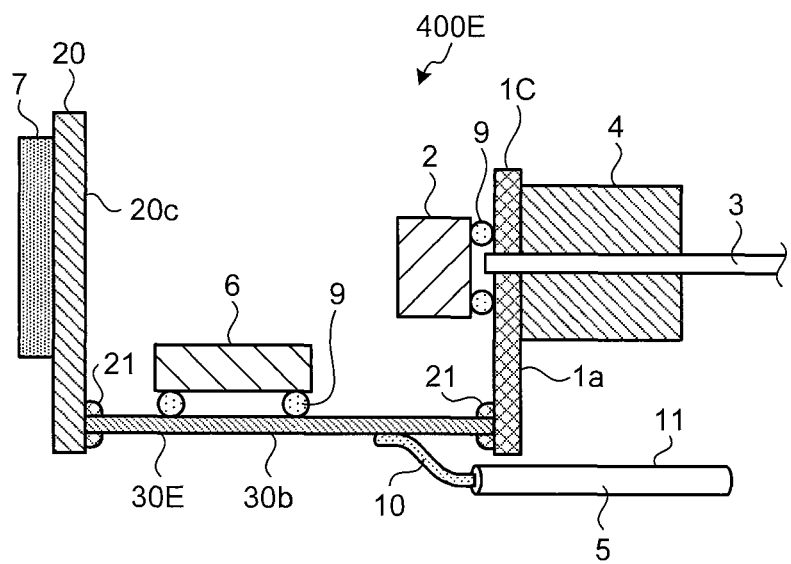
FIG. 24 is a cross-sectional view of an optical transmission module according to a fifth modification of the fourth embodiment.

In an optical transmission module 400E according to a fifth modification of the fourth embodiment, similarly to the fourth modification, the third substrate, the first substrate, and the second substrate are connected without through the connection portion. FIG. 24 is a cross-sectional view of the optical transmission module according to the fifth modification of the fourth embodiment of the present invention In the optical transmission module 400E according to the fifth modification, an end of a third substrate 30E is connected with the adhesive 21 to the surface of the first substrate 1C on which the VCSEL 2 is mounted so that the first substrate 1C and the third substrate 30E are perpendicular to each other. In addition, an end of the third substrate 30E is connected with the adhesive 21 to the back side of the surface of the second substrate 20 on which the image sensor 7 is mounted so that the second substrate 20 and the third substrate 30E are perpendicular to each other. It is noted that, in the fifth modification of the fourth embodiment, the VCSEL-driving IC 6 is connected to the second plane 30b of the third substrate 30E, but the VCSEL-driving IC 6 may be mounted on the surface of the first substrate 1C on which the VCSEL 2 is mounted.

Sixth Modification of Fourth Embodiment

Figure 25:
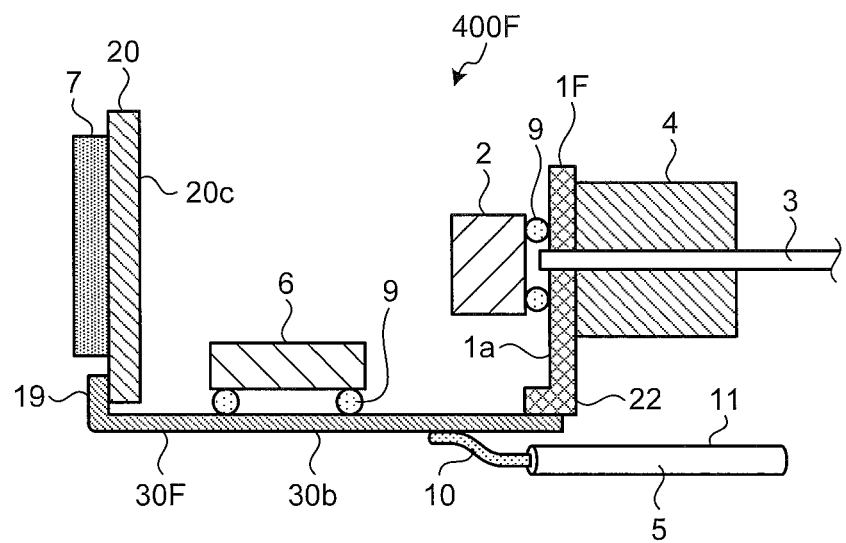
FIG. 25 is a cross-sectional view of an optical transmission module according to a sixth modification of the fourth embodiment.

In an optical transmission module 400F according to a sixth modification of the fourth embodiment, each of the first substrate and the third substrate has a connection portion. FIG. 25 is a cross-sectional view of the optical transmission module according to the sixth modification of the fourth embodiment of the present invention. In the optical transmission module 400F according to the sixth modification, a first substrate 1F has a connection portion 22 standing perpendicular to the first plane 1a on which the VCSEL 2 is mounted. The connection portion 22 is connected on a third substrate 30F so that the first substrate 1F and the third substrate 30F are perpendicular to each other. Further, the connection portion 19 standing perpendicular to the second plane 30b of the third substrate 30F is connected to the surface of the second substrate 20 on which the image sensor 7 is mounted so that second substrate 20 and the third substrate 30F are perpendicular to each other. It is noted that the connection portion 22 may be connected to the back side of the surface of the third substrate 30F on which the VCSEL-driving IC 6 is mounted, and the connection portion 19 may be connected to the surface or the back side of the surface of the second substrate 20 on which the image sensor 7 is mounted. Further, the connection portion 22 may be connected to the surface of the third substrate 30F on which the VCSEL-driving IC 6 is mounted, and the connection portion 19 may be connected to the back side of the surface of the second substrate 20 on which the image sensor 7 is mounted. Still further, in the sixth modification of the fourth embodiment, the VCSEL-driving IC 6 is connected to the second plane 30b of the third substrate 30F, but the VCSEL-driving IC 6 may be connected to the surface of the first substrate 1F on which the VCSEL 2 is mounted.

Seventh Modification of Fourth Embodiment

Figure 26:
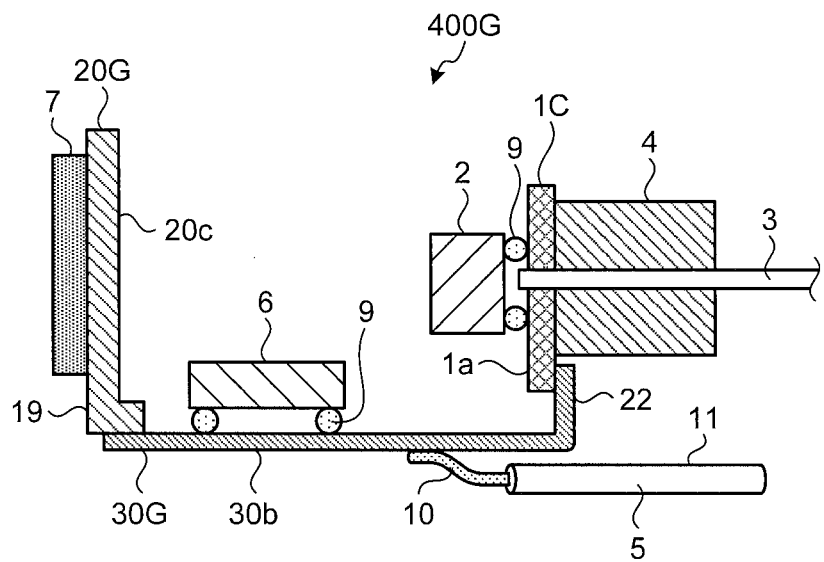
FIG. 26 is a cross-sectional view of an optical transmission module according to a seventh modification of the fourth embodiment.

In an optical transmission module 400G according to a seventh modification of the fourth embodiment, each of the second substrate and the third substrate has a connection portion. FIG. 26 is a cross-sectional view of the optical transmission module according to the seventh modification of the fourth embodiment of the present invention. In the optical transmission module 400G according to the seventh modification, a third substrate 30G has the connection portion 22 standing perpendicular to the second plane 30b on which the VCSEL-driving IC 6 is mounted. The connection portion 22 is connected to the back side of the surface of the first substrate 1C on which the VCSEL 2 is mounted so that the first substrate 1C and the third substrate 30G are perpendicular to each other. Further, the connection portion 19 standing perpendicular to the third plane 20c of a second substrate 20G is connected to the surface of the third substrate 30G on which the VCSEL-driving IC 6 is mounted so that the second substrate 20G and the third substrate 30G are perpendicular to each other. It is noted that, the connection portion 22 may be connected to the surface of the first substrate 1C on which the VCSEL 2 is mounted, and the connection portion 19 may be connected to the surface or the back side of the surface of the third substrate 30G on which the VCSEL-driving IC 6 is mounted. Further, the connection portion 22 may be connected to the back side of the surface of the first substrate 1C on which the VCSEL 2 is mounted, and the connection portion 19 may be connected to the back side of the surface of the third substrate 30G on which the VCSEL-driving IC 6 is mounted. It is noted that, in the seventh modification of the fourth embodiment, the VCSEL-driving IC 6 is connected to the second plane 30b of the third substrate 30G, but the VCSEL-driving IC 6 may be mounted on the surface of the first substrate 1C on which the VCSEL 2 is mounted.

Fifth Embodiment

Figure 27:
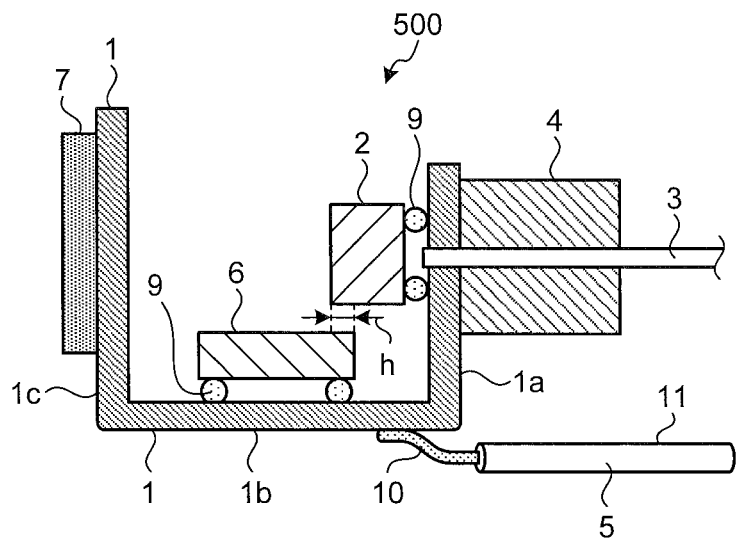
FIG. 27 is a cross-sectional view of an optical transmission module according to a fifth embodiment.

An optical transmission module 500 according to a fifth embodiment is different from the optical transmission module 100 according to the first embodiment in that the VCSEL 2 mounted on the first plane 1a and the VCSEL-driving IC 6 mounted on the second plane 1b are disposed to overlap each other in the direction of the optical axis of the optical fiber 3. FIG. 27 is a cross-sectional view of the optical transmission module according to the fifth embodiment of the present invention.

In the optical transmission module 500 according to a fifth embodiment, the VCSEL 2 mounted on the first plane 1a and the VCSEL-driving IC 6 mounted on the second plane 1b are disposed to overlap each other by a length h in the direction of the optical axis of the optical fiber 3.

In the optical transmission module 500 according to the fifth embodiment, similarly to the first embodiment, the resist is removed from the bent portion of the FPC so that resist peeling caused by bending the FPC can be prevented, and the bent portion is bonded and secured with the adhesive so that the first plane 1a and the second plane 1b, and the second plane 1b and the third plane 1c are perpendicular to each other, respectively, so that variation in bending angle of the FPC can be minimized. Further, the VCSEL 2 and the VCSEL-driving IC 6 are disposed to overlap each other in the direction of the optical axis of the optical fiber, so that the optical transmission module 500 can have a further reduced length (length in the direction of the optical axis of the optical fiber 3). Further, the cable 5 is connected to the back side of the second plane 1b in parallel with the optical axis of the optical fiber 3, therefore the optical transmission module 500 can have a reduced height (diameter). In the optical transmission module 500 according to the fifth embodiment, the VCSEL, the VCSEL-driving IC, and the image sensor are mounted on one substrate, therefore, a manufacturing process of the optical transmission module can be simplified.

First Modification of Fifth Embodiment

Figure 28:
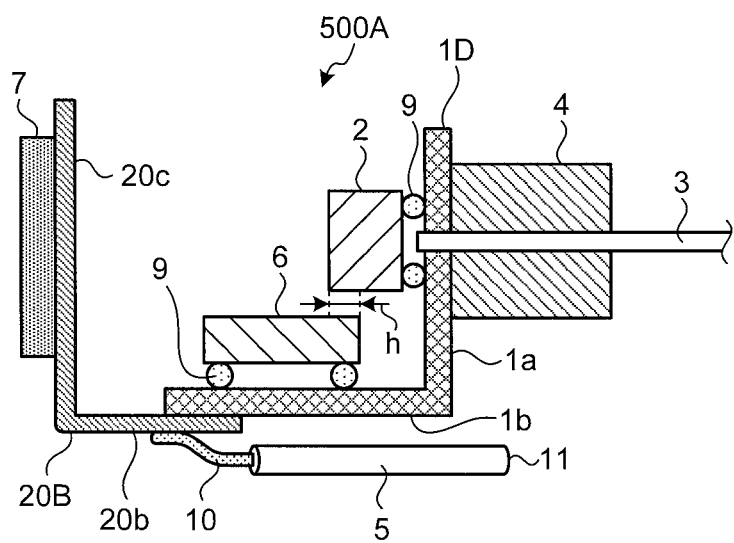
FIG. 28 is a cross-sectional view of an optical transmission module according to a first modification of the fifth embodiment.

An optical transmission module 500A according to a first modification of the fifth embodiment is different from the fifth embodiment in that the VCSEL 2, the VCSEL-driving IC 6, and the image sensor 7 are mounted on the first substrate and the second substrate. FIG. 28 is a cross-sectional view of the optical transmission module according to the first modification of the fifth embodiment of the present invention. In the optical transmission module 500A according to the first modification, the first substrate 1D has the first plane 1a on which the VCSEL 2 is mounted, and the second plane 1b on which the VCSEL-driving IC 6 is mounted, and which is perpendicular to the first plane 1a. The second substrate 20B has a third plane 20c on which the image sensor 7 is mounted, and the second plane 20b perpendicular to the third plane. In the optical transmission module 500A according to the first modification, the second plane 1b of the first substrate 1D is connected to the second plane 20b of the second substrate 20B so that the second plane 1b overlaps the second plane 20b. In the optical transmission module 500A, similarly to the fifth embodiment, the VCSEL 2 and the VCSEL-driving IC 6 are disposed to overlap each other, so that the optical transmission module 500A can have a further reduced length (length in the direction of the optical axis of the optical fiber 3). It is noted that the second plane 20b of the second substrate 20B may be connected to the second plane 1b of the first substrate 1D so that the second plane 20b overlaps the second plane 1b. Further, the cable 5 is connected to the second plane 20b of the second substrate 20B in parallel with the optical axis of the optical fiber 3 in order to reduce a noise of the signal transmitted to the image sensor 7, but the cable 5 may be connected to the second plane 1b of the first substrate 1D.

Second Modification of Fifth Embodiment

Figure 29:
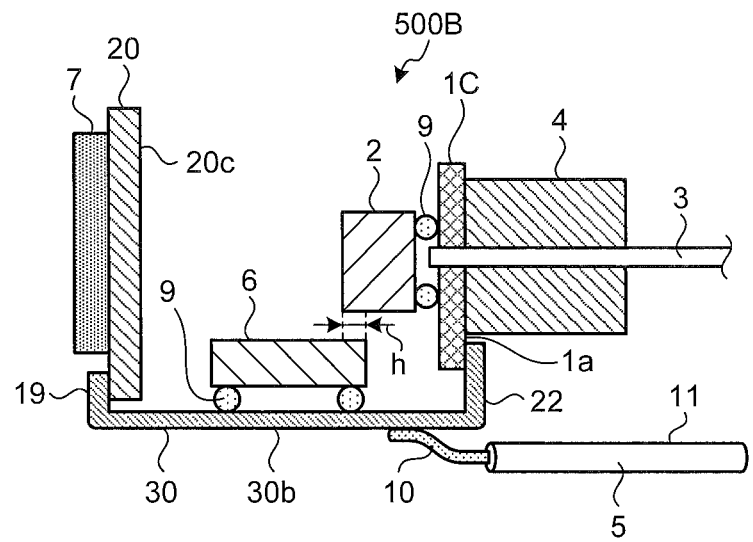
FIG. 29 is a cross-sectional view of an optical transmission module according to a second modification of the fifth embodiment.

An optical transmission module 500B according to a second modification of the fifth embodiment is different from the fifth embodiment in that the VCSEL 2, the VCSEL-driving IC 6, and the image sensor 7 are mounted on the first substrate, the second substrate, and the third substrate, respectively. FIG. 29 is a cross-sectional view of the optical transmission module according to the second modification of the fifth embodiment of the present invention. In the optical transmission module 500B according to the second modification, the third substrate 30 has the plate-shaped second plane 30b, and the connection portions 19 and 22 standing perpendicular to the second plane 30b. The connection portion 19 is connected to a surface of the second substrate 20 on which the image sensor 7 is mounted, and the connection portion 22 is connected to the back side of the surface of the first substrate 1C on which the VCSEL 2 is mounted. In the optical transmission module 500B, similarly to the fifth embodiment, the VCSEL 2 and the VCSEL-driving IC 6 are disposed to overlap each other, so that the optical transmission module 500B can have a further reduced length (length in the direction of the optical axis of the optical fiber 3). It is noted that the connection portion 19 may be connected to the back side of the surface of the second substrate 20 on which the image sensor 7 is mounted, and the connection portion 22 may be connected to the surface or the back side of the surface of the first substrate 1C on which the VCSEL 2 is mounted. Further, the connection portion 19 may be connected to the surface of the second substrate 20 on which the image sensor 7 is mounted, and the connection portion 22 may be connected to the surface of the first substrate 1C on which the VCSEL 2 is mounted.

Third Modification of Fifth Embodiment

Figure 30:
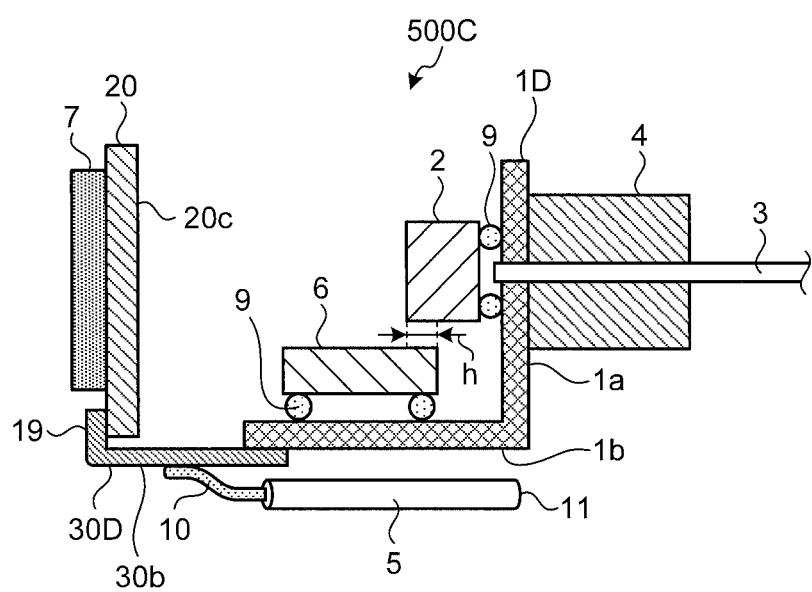
FIG. 30 is a cross-sectional view of an optical transmission module according to a third modification of the fifth embodiment.

An optical transmission module 500C according to a third modification of the fifth embodiment is different from the fifth embodiment in that the optical transmission module 500C has the first substrate, the second substrate, and the third substrate, and the VCSEL 2, the VCSEL-driving IC 6, and the image sensor 7 are mounted on the first substrate and the second substrate. FIG. 30 is a cross-sectional view of the optical transmission module according to the third modification of the fifth embodiment of the present invention. In the optical transmission module 500C according to the third modification, the first substrate 1D has the first plane 1a on which the VCSEL 2 is mounted, and the second plane 1b on which the VCSEL-driving IC 6 is mounted, and which is perpendicular to the first plane 1a. The third substrate 30D has the second plane 30b, and the connection portion 19 standing perpendicular to the second plane 30b. The second plane 1b of the first substrate 1D is connected to the second plane 30b of the third substrate 30D so that the second plane 1b overlaps the second plane 30b. Further, in the optical transmission module 500C, the connection portion 19 of the third substrate 30D is connected to the surface of the second substrate 20 on which the image sensor 7 is mounted, and similarly to the fifth embodiment, the VCSEL 2 and the VCSEL-driving IC 6 are disposed to overlap each other, so that the optical transmission module 500C can have a further reduced length (length in the direction of the optical axis of the optical fiber 3). It is noted that the second plane 30b may be connected on the second plane 1b, and the connection portion 19 may be connected to the surface or the back side of the surface of the second substrate 20 on which the image sensor 7 is mounted. Further, the second plane 1b may be connected on the second plane 30b, and the connection portion 19 may be connected to the back side of the surface of the second substrate 20 on which the image sensor 7 is mounted. Further, the cable 5 is connected to the second plane 30b of the third substrate 30D in parallel with the optical axis of the optical fiber 3, but the cable 5 may be connected to the second plane 1b of the first substrate 1D.

According to some embodiments, an optical transmission module and an imaging device can be provided. The optical transmission module can be reduced in size by mounting a photoelectric conversion element and a photoelectric conversion element-driving IC to a substrate having at least a first plane and a second plane perpendicular to each other, connecting an optical fiber perpendicular to a back side of the first plane on which the photoelectric conversion element is mounted, and connecting a cable to the second plane in parallel with an optical axis of the optical fiber.

As described above, the optical transmission module and the imaging device according to some embodiments are suitable for use in high-speed signal transmission between the signal processing device and the image sensor having a large number of pixels. Further, the optical transmission module according to the present invention is particularly suitable for use in, for example, an endoscope or an ultrasonic imaging system (ultrasonic endoscope) performing high-speed data communication and required to be reduced in size.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An optical transmission module comprising:
   a photoelectric conversion element configured to convert an electrical signal to an optical signal;
   a photoelectric conversion element-driving IC configured to drive the photoelectric conversion element;
   an optical fiber configured to transmit the optical signal emitted from the photoelectric conversion element;
   a guide holding member configured to position and hold the optical fiber;
   a cable configured to supply power or a signal to at least one of the photoelectric conversion element and the photoelectric conversion element-driving IC; and
   a single flexible printed circuit substrate on which the photoelectric conversion element and the photoelectric conversion element-driving IC are directly mounted, wherein
   the single flexible printed circuit substrate has at least a first plane and a second plane,
   the first plane and the second plane are perpendicular to each other,
   the single flexible printed circuit substrate has a bent portion,
   the single flexible printed circuit substrate is bent at the bent portion to form the first plane and the second plane,
   the photoelectric conversion element is mounted on the first plane,
   the optical fiber is connected to a back side of the first plane through the guide holding member such that an optical axis of the optical fiber is perpendicular to the first plane, and
   the cable is directly connected to a back side of the second plane, the photoelectric conversion element, the photoelectric conversion element-driving IC and the guide holding member are not mounted on the backside of the second plane, and the back side of the second plane is perpendicular to the back side of the first plane such that the cable is in parallel with the optical axis of the optical fiber.

2. The optical transmission module according to claim 1, wherein
   the single flexible printed circuit substrate includes a first substrate disposed perpendicular to the optical axis of the optical fiber, and a second substrate disposed parallel to the optical axis of the optical fiber, and
   the first and second substrates are connected to each other.

3. The optical transmission module according to claim 1, wherein the photoelectric conversion element-driving IC is mounted such that an upper surface of the photoelectric conversion element-driving IC is parallel to the optical axis of the optical fiber.

4. The optical transmission module according to claim 1, wherein the photoelectric conversion element-driving IC is mounted such that an upper surface of the photoelectric conversion element-driving IC is perpendicular to the optical axis of the optical fiber.

5. The optical transmission module according to claim 3, wherein the photoelectric conversion element and the photoelectric conversion element-driving IC are mounted to overlap each other in a direction of the optical axis of the optical fiber.

6. An imaging device comprising:
   a photoelectric conversion element configured to convert an electrical signal to an optical signal;
   a photoelectric conversion element-driving IC configured to drive the photoelectric conversion element;
   an optical fiber configured to transmit the optical signal emitted from the photoelectric conversion element;
   a guide holding member configured to position and hold the optical fiber;

a cable configured to supply power or a signal to at least one of the photoelectric conversion element and the photoelectric conversion element-driving IC;

an image sensor configured to acquire an image signal upon imaging; and a single flexible printed circuit substrate on which the photoelectric conversion element, the photoelectric conversion element-driving IC, and the image sensor are directly mounted, wherein the single flexible printed circuit substrate has a first plane, a second plane, and a third plane, the first plane and the second plane are perpendicular to each other, and the second plane and the third plane are perpendicular to each other, the first plane and the third plane are parallel to each other, the single flexible printed circuit substrate has a first bent portion and a second bent portion, the single flexible printed circuit substrate is bent at the first bent portion to form the first plane and the second plane, and is bent at the second bent portion to form the second plane and the third plane, the photoelectric conversion element is mounted on the first plane, the image sensor is mounted on the third plane, the optical fiber is connected to a back side of the first plane through the guide holding member such that an optical axis of the optical fiber is perpendicular to the first plane, and the cable is directly connected to a back side of the second plane, the photoelectric conversion element, the photoelectric conversion element-driving IC and the guide holding member are not mounted on the backside of the second plane, and the back side of the second plane is perpendicular to the back side of the first plane such that the cable is in parallel with the optical axis of the optical fiber.

7. The imaging device according to claim 6, wherein
the single flexible printed circuit substrate includes a first substrate having at least the first plane on which the photoelectric conversion element is mounted, and a second substrate having at least the third plane on which the image sensor is mounted, and
the first and second substrates are connected to each other.

8. The imaging device according to claim 7, wherein
the single flexible printed circuit substrate includes: the first substrate having the first plane on which the photoelectric conversion element is mounted, and having a plane perpendicular to the first plane; and the second substrate having the third plane on which the image sensor is mounted, and having a plane perpendicular to the third plane,
the first substrate and the second substrate are connected to each other, and
the cable is connected to the second substrate in parallel with the optical axis of the optical fiber.

* * * * *